United States Patent [19]

Schwartz

[11] Patent Number: 5,599,664

[45] Date of Patent: Feb. 4, 1997

[54] METHOD FOR CHARACTERIZING POLYMER MOLECULES OR THE LIKE

[75] Inventor: David C. Schwartz, Baltimore, Md.

[73] Assignee: New York University, New York, N.Y.

[21] Appl. No.: 162,379

[22] Filed: Dec. 7, 1993

Related U.S. Application Data

[63] Continuation of Ser. No. 333,531, Apr. 5, 1989, abandoned.

[51] Int. Cl.$^6$ .............................. C12Q 1/68; C12P 19/34; C25B 1/00; C12N 15/00
[52] U.S. Cl. .................. 435/6; 435/91.1; 435/172.3; 435/270; 435/820; 435/968; 436/543; 436/545; 436/546; 436/800; 436/94; 204/450; 536/23.1; 536/24.3; 536/25.3; 935/76; 935/77
[58] Field of Search ........................... 435/6, 172.3, 270, 435/91.1, 183, 820, 968; 204/182.8; 935/1, 19, 76, 77; 436/543–546, 800, 94; 536/23.1, 24.3–24.32, 25.3

[56] References Cited

U.S. PATENT DOCUMENTS

| | | | |
|---|---|---|---|
| 4,473,452 | 9/1984 | Cantor e talil | 204/180 |
| 4,695,548 | 9/1987 | Cantor et al. | 435/6 |
| 4,737,251 | 4/1988 | Carle et al. | 204/182.8 |
| 4,870,004 | 9/1989 | Conroy et al. | 204/182.8 |
| 5,059,294 | 10/1991 | Lizardi | 204/182.8 |
| 5,405,519 | 4/1995 | Schwartz | 204/299 R |

OTHER PUBLICATIONS

Yanagida et al., "Dynamic Behaviors of DNA Molecules in Solution . . . ", *Cold Sprg. Hrbr. Symp. Quant. Biol.* 47:177–187, 1983.
Zubay, *Biochemistry*, pp. 918–919, 1988.
Kucherlapati et al., *Genetic Recombination*, pp. 92–106, 1988.
Smith et al., "Observation of Individual DNA Molecules Undergoing Gel Electrophoresis", *Science* 243:203–206, Jan. 13, 1989.
Carle et al., "Electrophoretic Separations of Large DNA Molecules . . . " *Science* 232:65–68, Apr. 4, 1986.
Dev et al., "Techniques for Chromosome Analysis", pp. 493–503, in *Techniques in Somatic Cell Genetics*, Edited by Shay, 1982.
Rampino, "The Physics of Gel Electrophoresis".
Stellwagen, "Effect of Pulsed and Reversing Electric Fields . . . " Biochem. 27:6417–6424, 1988.

(List continued on next page.)

*Primary Examiner*—Stephanie W. Zitomer
*Assistant Examiner*—Bradley L. Sisson
*Attorney, Agent, or Firm*—Cushman Darby & Cushman, L.L.P.

[57] ABSTRACT

A method for observing and determining the size of individual particles and for determining the weight distribution of a sample containing particles of varying size, which involves placing a deformable or nondeformable particle in a medium, subjecting the particle to an external force, thereby causing conformational and/or positional changes, and then measuring these changes. Preferred ways to measure conformational and positional changes include: (1) determining the rate at which a deformable particle returns to a relaxed state after termination of the external force, (2) determining the rate at which a particle becomes oriented in a new direction when the direction of the perturbing force is changed, (3) determining the rate at which a particle rotates, (4) measuring the length of a particle, particularly when it is at least partially stretched, or (5) measuring at least one diameter of a spherical or ellipsoidal particle. Measurements of relaxation, reorientation, and rotation rates, as well as length and diameter can be made using a light microscope connected to an image processor. Particle relaxation, reorientation and rotation also can be determined using a microscope combined with a spectroscopic device. The invention is particularly useful for measuring polymer molecules, such as nucleic acids, and can be used to determine the size and map location of restriction digests. Breakage of large polymer molecules mounted on a microscope slide is prevented by condensing the molecules before mounting and unfolding the molecules after they have been placed in a matrix.

28 Claims, 6 Drawing Sheets

OTHER PUBLICATIONS

Poddar, et al. "Chromosome analysis by two-dimensional fingerprinting" *Gene,* 49 (1986) pp. 93–102.

Woolf, et al. "mapping genomic organization by field inversion and two-dimensional gel electrophoresis" *Nucleic Acid Research,* vol. 16, No. 9, (1988) pp. 3863–3875.

Roemling, et al. "A physical genome map of Pseudomonas aeruginosa" *The EMBO Journal,* vol. 8 No. 13 (1989) pp. 4081–4089.

Chattoraj et alii, *Journal of Molecular Biology,* (1978) 121, 327–337.

Yanagida et alii, Cold Spring Hrbr. Synp. *Quant, Biol.,* (1983) 47, 177–187.

Sommer and Tautz, *Nucleic Acids Research,* (1989) vol. 17, No. 16, 6749.

Manuelidis et al, *Biol. Abstr.* 76 (4):2940, Ref. No. 27153, *J. Cell. Biol.* 95(2 Part1):619–625, 1982.

Chattoraj et al., "DNA Condensation with Polyamines", *J. Mol. Biol.* 121:327–337 (1978).

Ohi et al., "Mapping of Mitochondrial 4S RNA Genes . . . by Electron Microscopy", *J. Mol. Biol.* 121:299–310, 1978.

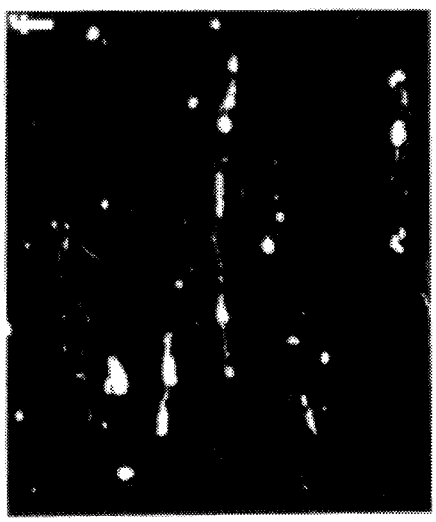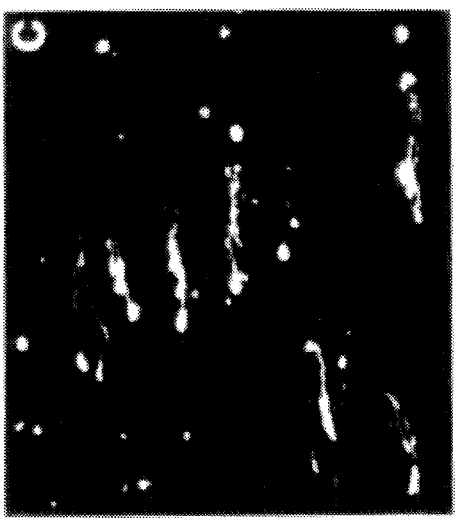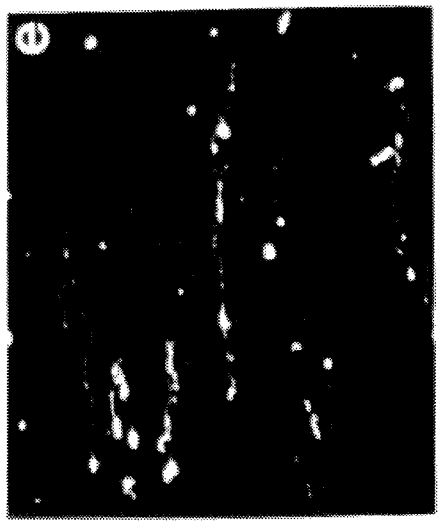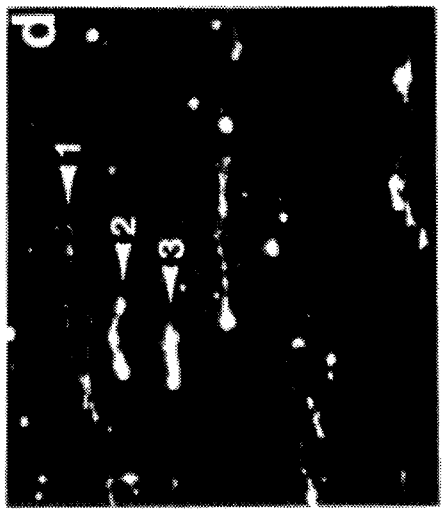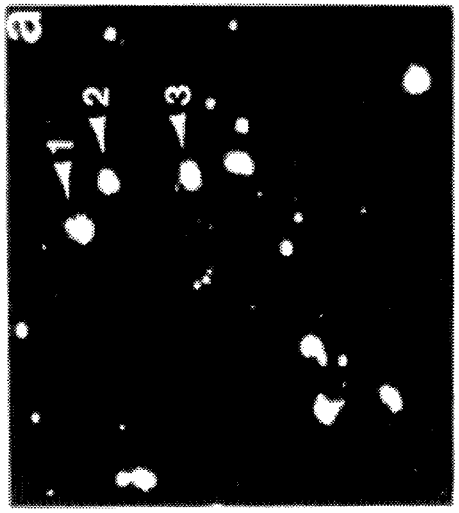

METHOD FOR CHARACTERIZING POLYMER MOLECULES OR THE LIKE

This is a continuation of application Ser. No. 07/333,531, filed on Apr. 5, 1989, which was abandoned upon the filing hereof.

BACKGROUND OF THE INVENTION

This invention was made with U.S. Government support under Contract No. GM 37277 awarded by the National Institute of General Medical Sciences of the United States Department of Health and Human Services.

This invention relates a method for characterizing polymer molecules or the like, for example, observing and determining the size of individual particles and determining the weight distribution of a sample containing particles of varying size. More particularly, this invention involves the use of microscopy and/or microscopy in combination with spectroscopic methods to characterize particles, such as by measuring their positional and conformational changes when they are subjected to an external force, and by measuring their length and diameter or radius. Such measurements include rates of relaxation, reorientation and rotation of particles subject to an external force, and measurements of length and diameter of particles before, during or after they are subjected to an external force.

Among other applications, these measurements are used to determine particle size. The invention is especially well suited to size polymer molecules in a polydisperse sample (e.g., a sample containing particles of varying size), when the particles have been placed in some type of medium, and is useful to measure very large molecules, such as large nucleic acid molecules which are subject to breakage when placed on a microscope slide using conventional methods.

Methods for determining the molecular weight distribution of a polydisperse sample of particles are useful in a variety of different fields. For example, in polymer chemistry, the properties of an oligomer are often dependent upon its molecular weight distribution. When a particular substance is found to exhibit favorable properties and the exact composition of the oligomer is not known, an analysis of the molecular weight distribution of the polymer is used for purposes of identification. In molecular biology, the molecular weight distribution of a polydisperse sample, such as a sample of DNA restriction enzyme digests, provides valuable information about the organization of the DNA. This information may be used to produce chromosome maps and extensive molecular genetics characterizations.

Traditionally, the molecular weight distribution of a sample of particles has been determined by measuring the rate at which particles which are subjected to a perturbing force move through an appropriate medium, e.g., a medium which causes the particles to separate according to size. A mathematical relationship is calculated which relates the size of particles and their migration rate through a medium when a specified force is applied. For example, in gel permeation chromatography, a well-known technique, a polymer to be characterized is dissolved in a solvent and the resulting solution is then passed through a column which has a cross-linked or porous gel polymer in the stationary phase. Large molecules will pass quickly through the gel, while the movement of smaller molecules will be hindered by their entry into the pores of the substance comprising the stationary phase. The molecular weight distribution of the sample is determined by measuring the content of the effluent from the column, e.g., by measuring the refractive index of the effluent over a period of time. Several limitations of gel permeation chromatography are that it cannot be used to separate DNA molecules larger than about 5 kb, and it can only be used for samples which are soluble in (at least one of) a limited number of suitable solvents.

Sedimentation is a well-known technique for measuring particle size, but, when applied to polymers, this method is limited to molecules with a maximum size of about 50–100 kilobases (kb). Attempting to measure larger molecules by this technique would probably result in underestimation of molecular size, mainly because the sedimentation coefficient is sensitive to centrifuge speed. (see Kavenoff et al., *Cold Spring Harbor Symp. Quantit. Biol.*, 38, 1 (1974).

Another popular method of separating polymer particles by size is by gel electrophoresis (see, e.g., Freifelder, *Physical Biochemistry*, W. H. Freeman (1976), which is particularly useful for separating restriction digests. In brief, application of an electric field to an agarose or polyacrylamide gel in which polymer particles are dissolved causes the smaller particles to migrate through the gel at a faster rate than the larger particles. The molecular weight of the polymer in each band is calibrated by a comparison of the migration rate of an unknown substance with the mobility of polymer fragments of known length. The amount of polymer in each band can be estimated based upon the width and/or color intensity (optical density) of the stained band, however, this type of estimate is usually not very accurate.

Pulsed field electrophoresis, developed by the present inventor and described in U.S. Pat. No. 4,473,452, the disclosure of which is hereby incorporated by reference and relied upon, is an electrophoretic technique in which the separation of large DNA molecules in a gel is improved relative to separation using conventional electrophoresis. According to this technique, deliberately alternated electric fields are used to separate particles, rather than the continuous fields used in previously known electrophoretic methods. More particularly, particles are separated using electric fields of equal strength which are transverse to each other, which alternate between high and low intensities out of phase with each other at a frequency related to the mass of the particles. The forces move the particles in an overall direction transverse to the respective directions of the fields. It should be noted here that the term "transverse" as used herein is not limited to an angle of, or close to, 90°, but includes other substantial angles of intersection.

One of the most significant problems with determining the weight of molecules by indirect measurement techniques, such as those described above, is that the parameters which are directly measured, e.g., migration rate, are relatively insensitive to small differences in molecular size. Thus, a precise determination of particle size distribution is difficult to obtain. The lack of precision may particularly be a problem when biological polymer samples, which tend to be unstable and contain single molecules inches in length, are involved.

While some of the known methods of determining particle size distribution in a polydisperse sample provide better resolution than others, few, if any, of the previously known techniques provide resolution as high as is needed to distinguish between particles of nearly identical size. Gel permeation chromatography and sedimentation provide resolution of only about $M^{1/2}$ (M=molecular weight). Standard agarose gel electrophoresis and polyacrylamide gel electrophoresis provide resolution varying as $-\log M$. Pulsed electrophoretic techniques are effective for separating extraordinarily large molecules, but do not provide much better resolution than standard electrophoresis. Thus, the ability to distinguish between particles of similar size, for example, particles differing in length by a fraction of percent, is quite limited when the above-described measurement techniques are used.

Under special experimental circumstances, DNA gel electrophoresis resolves a polymer mixture to a resolution of $M^1$. However, this degree of accuracy is only achieved when variables such as gel concentration and field strength are carefully controlled.

Particles of higher mass (i.e., up to approximately 600 kb) can be resolved using conventional gel electrophoresis by reducing the gel concentration to as low as 0.035% and reducing field strength, however, there are drawbacks to this method. Most notably, the dramatic reduction in gel concentration results in a gel which is mechanically unstable, and less sample can be loaded. An electrophoretic run to resolve very large DNA molecules using a reduced gel concentration and field strength may take a week or more to complete. Furthermore, a reduced gel concentration is not useful to separate molecules in a sample having a wide range of particle sizes, because separation of small molecules is not achieved. Thus, if a sample containing molecules having a wide range of sizes is to be separated, several electrophoretic runs may be needed, e.g., first, a separation of the larger molecules and then further separation of the smaller molecules.

Other particle measurement techniques known in the art are useful for sizing certain molecules which are present in a bulk sample, (e.g., the largest molecules in the sample, or the average molecular size) but are impractical for measuring many polymers of varying length in a given sample. The viscoelastic recoil technique, (see Kavenoff et al, "Chromosome-sized DNA molecules from Drosophila," *Chromosoma* 41, 1 (1973)) which is well known in the art, involves stretching out coiled molecules in a solvent flow field (e.g., a field which is created when fluid is perturbed between two moving plates) and determining the time required for the largest molecule to return to a relaxed state. Relaxation time is measured by watching the rotation of a concentric rotor which moves during the time of relaxation. While this technique is quite precise in that sample determinations vary as $M^{1.66}$ when applied to large DNA molecules, it is not useful for sizing molecules other than the largest molecule in the sample.

Using light scattering techniques, which are known in the art, (e.g., quasi-elastic light scattering), the size and shape of particles are determined by a Zimm plot, a data analysis method which is known in the art. With these techniques, size dependence varies as $M^1$. Light scattering requires that the solution in which the molecules to be measured are placed is pure, that is, without dust or other contamination, and it is therefore unsuitable for sizing a DNA sample. Furthermore, it is not useful for sizing molecules as large as many DNA molecules, and is useful only for determining the average weight of particles in a sample, not the weight distribution of a sample with particles of various sizes.

Yet another particle measuring technique which is known in the art for measuring individual molecules provides measurements of particle size having limited accuracy. The average size and shape of individual, relaxed DNA molecules has been determined by observing the molecules under a fluorescence microscope, and measuring the major and minor axes of molecules having a spherical or ellipsoid shape (see Yanagida et al, *Cold Spring Harbor Symp.* *Quantit. Biol.* 47, 177, (1983)). The technique described in the above-cited reference is performed in a free solution, without perturbation of the molecules.

The movement of small DNA molecules during electrophoresis has been observed (see Smith et al. *Science*, 243, 203 (1989)). The methods disclosed in this publication are not suitable for observation of very large DNA molecules, and techniques for measuring molecules are not discussed.

It is noted that practical weight determinations of particles such as polymer molecules depend not only upon maximizing the size dependencies of the directly measured parameters, but also upon factors such as the amount of sample needed, the time required to complete an analysis, and the accuracy of measurements. Gel permeation chromatography can be time-consuming and requires a large amount of sample. Methods such as conventional gel electrophoresis can be relatively time-consuming, require moderate amounts of sample, and cannot size very large DNA molecules.

SUMMARY OF THE INVENTION

Accordingly, it is an object of the present invention to provide a method for effectively characterizing polymer molecules and the like, for example, determining the size of individual particles or the weight distribution of a polydisperse sample of particles.

Another object of this invention is to determine particle size using a method which provides better resolution than methods known in the prior art.

Yet another object of this invention is to provide a method for observing large molecules or other large particles, (including molecules too large to size using any other methodology), determining their size, and determining the molecular weight distribution of a sample containing large molecules.

A further object of this invention is to provide a faster and more efficient method for determining the size of individual particles and the weight distribution of a sample of particles.

Another object of this invention is to size one or more particles using an extremely sensitive method, e.g., one which can use an amount of sample as small as a single particle.

Yet another object of this invention to provide accurate size information for a polydisperse sample containing particles having a wide range of sizes, and to provide this information more quickly than by using previously known techniques.

These and other objects of the invention will be apparent from the discussion which follows.

Broadly described, the method of the invention involves characterizing individual particles, including deformable and non-deformable particles in a polydisperse sample by placing the particles in a medium, applying an external force to the particles, thereby causing physical changes, particularly conformational and/or positional changes, and then observing and measuring these changes. This method is useful for characterizing polymer molecules of a variety of sizes, including the smallest molecules which are detected by a suitable microscope (the microscope optionally may be attached to a spectroscopic apparatus and thus molecules too small to be visualized may still be detected), and large polymers, which may be up to several inches in length when stretched to a linear conformation. Shear sensitive molecules (e.g., large molecules), which cannot be placed on a microscope slide without breaking when conventional techniques are used, are measured according to this invention by collapsing (condensing) the molecules before they are placed in the medium and then uncollapsing them after placement in the medium. This invention is useful for characterizing many types of particles which can be visualized or detected under a light microscope. Several non-limiting examples include polysaccharides, polypeptides and proteins.

Deformable particles are particles which have a tendency to change conformation (shape) as well as position when they are subjected to an external force. Nondeformable particles tend to have a substantially stable conformation even when subjected to an external force, but may undergo changes in position. Deformable particles are usually reversibly deformable, e.g., they change conformation when an external force is applied, and then return to a configuration comparable to their original shape when application of the force is terminated.

This invention is particularly useful for measuring polymer molecules which are folded, coiled or possibly even supercoiled when in a relaxed state, and are subject to conformational changes such as stretching, bending, twisting, contracting, etc., and positional changes such as rotating, translating etc. This invention is particularly useful when an external force is applied to molecules which are in some type of medium. However, if a free solution is used, application of an external force may not be needed to cause the molecules to change conformation or position.

Particles which are large enough to be seen using a microscope are measured by visualization, e.g., by direct observation of a microscopic image. Particles may, alternatively, be measured using microscopy combined with any suitable spectroscopic technique, particularly if the particles are too small to be imaged (viewed with acceptable resolution).

Several non-limiting examples of useful spectroscopic methods include using polarized radiation as generated by a laser combined with measurement of refractive index or fluorescence dichroism, or using sensitive video cameras such as cooled charged coupled devices, silicon intensified target devices, and micro-channel plate detectors.

Samples containing a mixture of both small and large particles, for example, small and large DNA molecules are sized rapidly, with each particle in the sample being measured simultaneously. The method of this invention involves measuring conformational and positional changes of individual, discrete molecules (or other particles), as contrasted to method known in the art, which characterize a sample in bulk. The method of this invention is applied to measure any number of particles, ranging from a single particle to a large number of particles. If a sample containing a large number of particles is measured, the number of particles which are observed at one time will depend in part upon the field of view of the microscope and the extent to which the particles are separated from each other. Viewing discrete, individual particles, or measuring their role of relaxation after applying an external force permits complete deconvolution or separation of measured parameters.

The medium used in this invention is any suitable material. Preferably the medium will hold relaxed particles in a relatively stationary position and yet permit movement of particles which are subjected to an external force. However, a free solution also may be used. For measurements of molecular movement, a suitable medium is any medium which will permit different particles to change conformation and position at different rates, depending upon their size, and perhaps upon their chemical composition.

For many uses of this invention, the preferred medium is a gel or a liquid. Preferably, the medium is anticonvective, but this is not absolutely necessary. The medium may or may not be inert. The choice of an appropriate medium will depend in part upon the size of the particles which are measured, the tendency for the particles to change position and shape, and the desired precision of the measurements. For example, when large molecules (or other particles of similar size) are measured, a gel with a large pore size is preferably used.

The external force applied to the particles is any force which causes the non-deformable or deformable particles to undergo changes in conformation or position. For example, the force may be an electric field, solvent flow field, or a magnetic field, but is not limited to these types. The force may vary in direction, duration and intensity. A particularly useful way to perturb the particles is by using electrophoresis.

The types of changes which are measured in this invention primarily include changes in conformation or shape, including stretching and relaxation rates, as well as length and diameter (or radius) measurements, and changes in position, including changes in orientation and rotation as well as translation within the medium. Particles may undergo changes in conformation or position, or both. Different types of changes are measured according to various embodiments of the invention.

The techniques for measuring conformational and positional changes include, but are not necessarily limited to, microscopy (alone), and microscopy combined with spectroscopy. Several non-limiting examples of useful spectroscopic techniques include birefringence, linear or circular dichroism, and detection of fluorescence intensity.

Particles which are large enough to be seen under a microscope can be measured by visualizing (imaging) the particles. As non-limiting examples, a light microscope or a scanning/tunneling microscope may be used. While particles may be viewed directly, it is useful to link the microscope to a low light sensitive video camera, connected to a computerized image processor (described in detail below) which records a series of photographs, even a motion picture, by digitizing the images which are received. The image processor may itself comprise a computer, or may be linked to a computer which processes data based upon the images. Use of a computerized apparatus enables the movement of each individual molecule to be measured simultaneously. Furthermore, the relationship of molecules to one another may be detected, and several different parameters of a single particle can be measured simultaneously.

Optionally, the microscope and image processor are connected to a spectroscopic apparatus. This technique is particularly useful for particles which are too small to be visualized, but is useful for sizing larger particles as well.

In order to transform measurements of change in conformation and position into size measurements, it is generally necessary to generate (or otherwise obtain) data relating to physical changes of particles of known size when the particles are subject to external forces. "Markers" are developed by measuring the parameters of molecules with known values of molecular weight. This information may be input into the computer in order to establish a relation between molecular weight and particular conformational and positional changes which are measured. Preferably, the markers are particles of similar structure to the particles of unknown size (e.g., both particles contain the similar chemical components), because rates of relaxation, reorientation and rotation may be dependent upon particle composition. However, this may depend upon several variables, e.g., polymer size, composition, etc., and thus it may not always be necessary for the "markers" to have a composition similar to that of the particles of unknown size.

Shear sensitive particles are particles which are subject to breaking when they are placed on a microscope slide using conventional methods. According to another aspect of this invention, such particles are collapsed into a higher density conformation before they are placed in a medium, in order to prevent breakage when the particles are mounted on a microscope slide. Once they have been placed in the medium, they can be uncollapsed and measured by the same methods as the smaller molecules.

In one embodiment of the invention, fluorescently stained, deformable molecules which are coiled, folded or otherwise configured in a relaxed, native conformation are placed in a medium and are temporarily deformed, or stretched by applying an external force. When application of the force is stopped, the relaxation time of the molecules (e.g., the time required for the molecules to return to their original, relaxed state) is determined by direct microscopic observation of molecular movement, or by a combination of microscopy and spectroscopy. Alternatively, the kinetics of stretching are measured by following the stretching of the molecule after initiation of the external force. Rate measurements are calculated in various ways, for example, by determining an amount of change per unit time. Rates of change for molecules of unknown size are determined based upon rates of molecules of known size, such as by interpolation or extrapolation.

As with the viscoelastic measurement technique known in the art, the relaxation time of particles in a liquid according to this embodiment varies as about $M^{1.66}$. In a gel, it is believed that resolution may be as high as $M^{2-4}$. This is based upon theoretical principles which show that molecules rotate in gels or confining matrices, and their relaxation time is much greater in a gel than in a solution (DeGennes, P. E., *Scaling Concepts in Polymer Physics,* Cornell University Press, N.Y. (1979).

In a second embodiment, the reorientation time of a deformable or non-deformable particle is measured. When particles are first subject to a perturbing force in one direction, and the direction of the perturbing force is then changed, for example, by 90°, small particles quickly reorient themselves and start a new migration along the new path. Larger particles, on the other hand, remain substantially immobile until they are reoriented in the direction of the electric field. Then, they too begin to move in the new direction. By that time, the smaller particles will have moved ahead. Measurements of the rate at which the position of a molecule changes with respect to an external force may be measured, for example, by measuring changes in position (e.g., lateral and/or rotational movement) per unit time.

In a third embodiment, the rate at which a particle rotates is determined when a series of external forces are applied. This method is particularly applicable to rod-shaped molecules, such as small DNA molecules, and elongated molecules which are maintained in a relatively uniform conformation. "Rotation time" according to this invention is the amount of time required for a molecule to undergo a positional rotation of a particular angular increment, for example, 360°, when a particular set of external forces are applied.

By periodically switching pulse direction, intensity and length, molecules are caused to move slightly back and forth as they are rotated. This facilitates rotation, and is analogous to the way in which an automobile is manipulated into or out of a parallel parking space by alternating backward and forward motion. However, unlike an automobile, a rod-shaped or coil molecule may bend somewhat as it rotates. A pulsing routine may also function to keep a deformable particle in a generally consistent conformation, in order to provide useful measurements, e.g., measurements which relate rotation time to molecular size.

Data for reorientation and/or rotation rates for particles of known size may be used to develop a relationship between reorientation and/or rotation rate and molecular size, which then may be used to determine the size of various polymer molecules of similar composition and unknown size, such as those which are present in a polydisperse sample. Reorientation and rotation rate may be determined using microscopy (preferably combined with image processing) to directly observe positional changes, or by combining microscopy with spectroscopic measurements. Thus, these embodiments are useful not only for mid-sized and large molecules, but also for molecules that are too small to be imaged with acceptable resolution.

In yet another embodiment of this invention, the length of a molecule or other particle which has been placed in a medium is directly measured using microscopy. This technique provides direct measurement of the molecular size of any number of molecules. This method generally involves observing the curvilinear length of deformed molecules which are in a stretched state, e.g., during the application of an external force, or soon after termination of a force which has stretched a molecule. However, this method also may be applied to non-deformable molecules having an elongated shape, and measurement of such molecules does not require application of an external force before measurements are made. Preferably this embodiment uses the same microscopy and imaging equipment as is described above.

In a fifth embodiment, the diameter (or radius) of molecules or other particles suspended in a medium is measured. Application of a perturbing force is optional, because the diameter of a deformable molecule is preferably measured when the molecule is in a relaxed state, and the molecule is spherical, ellipsoidal or globular in shape. This embodiment may be used to measure particles which are deformable or non-deformable, and involves the use of a light microscope attached to a computerized imaging device.

These five embodiments may be combined such that some or all of the above-mentioned parameters are measured simultaneously for one or more molecules.

A sixth embodiment of the invention is directed particularly to sizing very large particles which tend to break if they are mounted on a microscope slide using conventional methods. In brief, this new technique involves collapsing the particles before they are placed in the medium, using an agent which causes them to condense, and then uncollapsing the particles after they have been placed in the medium. The molecules are then sized according to the method of embodiments one to five. The method for chemically collapsing molecules also may be used when it is desirable to place a large number of molecules in a small area, such as in microinjection, even if the molecules are not large or shear sensitive.

This invention provides a novel technique for mapping nucleic acid molecules. For example, when a nucleic acid is placed in a matrix and digested, the fragments are ordered by the computerized apparatus, and are sized by the methods described above. Thus, the order of the digests is quickly and accurately determined.

A further aspect of this invention provides for sequencing nucleic acid molecules by hybridizing probes to portions of a molecule. A nucleic acid is placed in a medium, to which suitable, desired probes are added. A recombinational enzyme may be added if necessary. Reaction is initiated by an appropriate means, for example, the addition of ATP (adenosine triphosphate) and magnesium ions. After the probes have hybridized they are detected by the methods described above, namely, microscopy (alone) or microscopy in combination with spectroscopy.

Thus, the present invention provides an accurate method of determining the size of individual particles and the weight distribution of a polydisperse sample of particles. Another important advantage of this invention over the techniques of the prior art is that the measurable parameters for each of the particles in a polydisperse sample, not just the largest particle, are determined. Additional advantages are that (1) only one molecule is needed, and the sample may be very small, e.g., may consist of only one, or only a few molecules (2) measurements may be based on one representative particle for each size in the sample, (3) the technique can be used for very large particles (particles too large to be measured by prior known methods), (4) data can be processed efficiently by computer, (5) measurements can be made more rapidly than methods known in the prior art (e.g. particularly as compared to slow electrophoresis processes, which may take several weeks), and (6) measurements are extremely accurate.

These and other advantages will become readily apparent from the detailed description which follows.

BRIEF DESCRIPTION OF THE DRAWINGS

FIGS. 4a, 4b, 4c, 4d, 4e, 4f, 4g, 4h and 4i show the DNA molecular conformational and positional changes when G bacteriophage molecules are subject to two sequential electric fields in different directions.

DETAILED DESCRIPTION OF THE INVENTION

Figure 1:
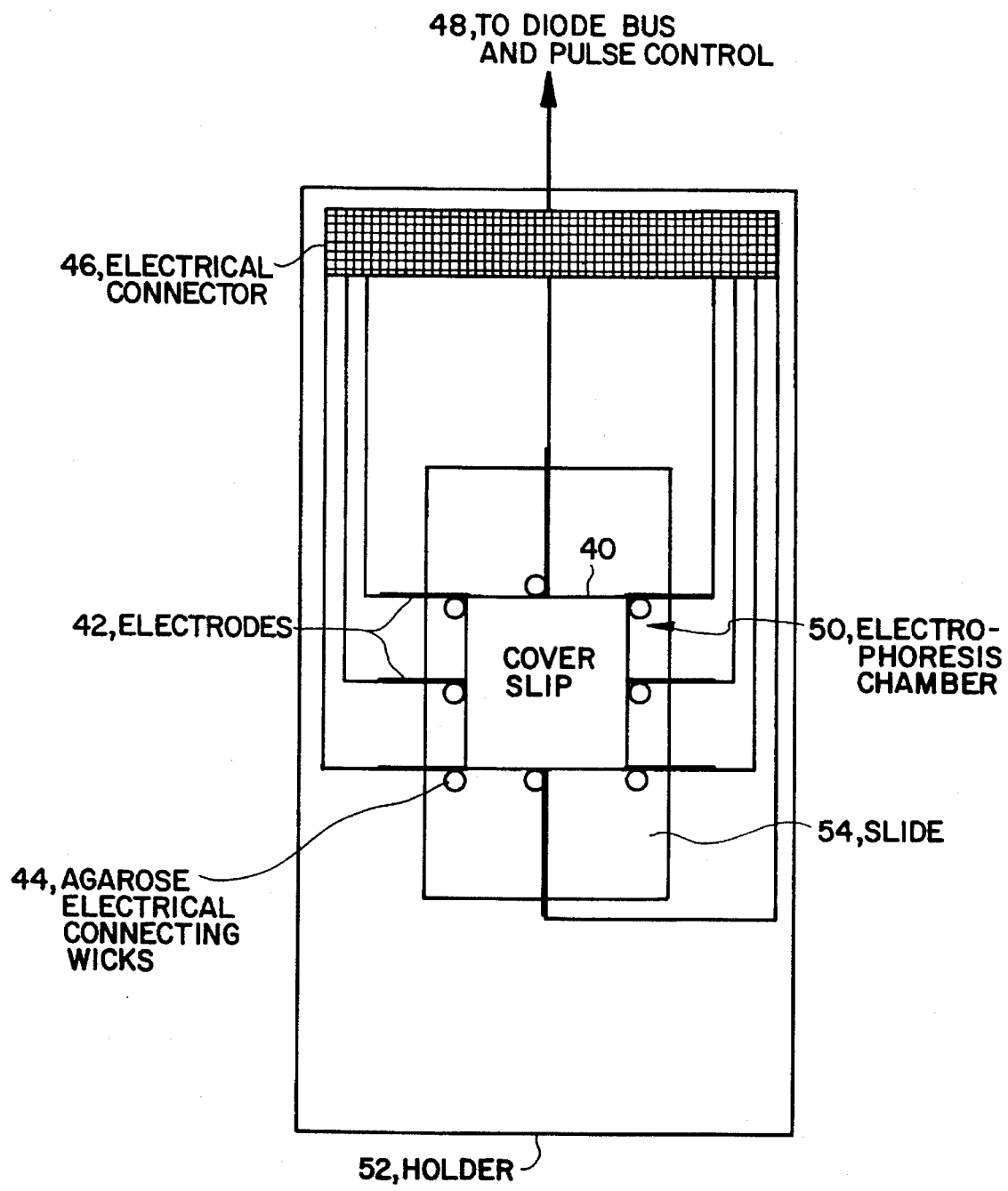
FIG. 1 is a schematic drawing of an electrophoretic microscopy chamber which is specifically adapted to fluorescence microscopy studies.

The process of the invention comprises placing particles in a medium to observe them and to measure their size. In several embodiments, particles are measured either during or after they are deformed or repositioned by an external force. The method of this invention is particularly suitable for examination of nucleic acids and other polymers which are coiled, or possibly even supercoiled, when they are in a relaxed (unperturbed) conformation.

Particles are placed in a medium, such as a solvent, powder, glass or gel. Other suitable mediums also may be used. The medium containing the particles may be placed on a microscopic slide, or may be positioned in some other manner so as to permit the molecules to be viewed under the microscope. The suitability of a particular medium may depend in part upon the measurement technique to be used. Measurement techniques requiring perturbation necessitate the use of a medium in which deformable particles are capable of changing conformation or position. When direct observations are made under a light microscope, a suitable medium also allows the particles to be viewed clearly. When microscopy is combined with birefringence measurements, a preferred medium prevents convection and enhances the size dependency of the observed signal. Additionally, the medium itself preferably is relatively free of significant birefringence during experimental conditions.

Characterization of particles based upon measurements of fluorescence intensity may be greatly enhanced using a matrix (e.g., a medium which partially confines particle movement) as the medium. For the method of this invention, the medium is preferably a solution or gel. Agarose and polyacrylamide gels are particularly well suited for use in this invention. Examples of suitable solvents include glycerol/water, polydextran/water, and organic solvents. However, these examples are not to be construed as limiting the scope of the invention.

In a preferred embodiment, agarose, a polysaccharide derived from agar having an average molecular weight of approximately 100,000 daltons, is dissolved in an aqueous buffer (typically a 1% solution) and allowed to cool, forming a rigid gel, similar to gelatin (as found in JELLO™). The gel matrix consists of a three-dimensional network of agarose polymer chains annealed to each other through hydrogen bonding. Heating the agarose gel will send it back into a fluid state, so that the gel is said to be reversible, just like gelatin. The important feature of an agarose gel is its extraordinarily large average pore size. Although the pore voids in agarose gel are presently not completely characterized, they are thought to be approximately 0.3 microns wide, and also contain smaller voids. Due to its large pore size and inertness, agarose is used in DNA gel electrophoresis, because it allows DNA molecules to stretch and move in a gel.

If a fluorescence microscope is to be used (or if fluorescence intensity is to be measured by other means), the particles generally are stained. Staining procedures are well known in the art. Useful stains or chromophores in this invention include, but are not limited to, ethidium bromide and 4',6-diamidino-2-phenyl-indole, dihydrochloride (DAPI). Most types of particles are stained at some time before they are imaged, and may be stained before or after they are placed in a medium.

When a deformable particle is placed in a medium and mounted on a slide, there are several possible ways to perturb the particle. Several non-limiting methods are as follows: (1) A particle is perturbed by the application of an electrical field, which moves a charged particle such as DNA through a matrix, distorting the coil conformation much as cookie dough distorts as it moves through a forming machine. This is the phenomenon involved in gel electrophoresis. (2) A flow field is created in the liquid agarose/DNA (or polymer of choice) and the particle-containing liquid is then gelled quickly with low temperature quenching, fast enough to prevent any significant coil relaxation. This method is useful whether or not the particle is charged. (3) Using the dielectrophoresis effect, uncharged molecules with field gradients (electric fields which change strength with position) are moved by distorting molecular electron clouds, thus inducing attractable dipoles. It is believed that dielectrophoresis could be used in a matrix such as agarose.

One of the advantages in using electrophoresis is that DNA particles are distinguished from other particles which may be present in the DNA-containing, medium because uncharged particles do not move in response to application of an electric field. Another possible way to distinguish DNA particles from others is to multiply the DNA.

The extent to which a molecule is to be perturbed, e.g., subjected to changes in conformation and/or position, before measurement may vary. For example, useful data on molecular relaxation is obtained even when a coiled molecule is perturbed such that it is only partially uncoiled.

As mentioned above, one of the preferred methods for perturbing molecules according to this invention involves electrophoresis. Any electrophoresis method suitable for use with a microscope may be used according to the present invention to perturb the particles. Electrophoresis may optionally serve another function in this invention. When a sample size is too large or complex to be viewed under a microscope all at once, molecules may be separated into sub-samples which then can be imaged separately.

Electrophoresis of molecules for viewing and measuring purposes may optionally use a chamber which is suitable for use in pulsed field electrophoresis, as described in U.S. Pat. No. 4,695,548, or for pulsed oriented electrophoresis, which is described below. These techniques are particularly useful in the event it is desirable to measure reorientation and/or rotation times, because of the ability to control field angles.

Pulsed Oriented Electrophoresis (POE), which was developed by the present inventor and is the subject of co-pending application Ser. No. 07/244,897, filed Sep. 15, 1988, was abandoned in favor of file wrapper continuation application Ser. No. 07/879,551, filed May 4, 1992, improves separation of polydisperse polymer molecules in a sample by using short electric pulses to create and vary field angles, with the effective field angle being defined by the vector sum of a series of pulses which may vary in duration, intensity and direction. Pulse times and pulse intensities are modulated to effect separation. POE is also useful for creating effective field angles during imaging. The needed instrumentation is readily adapted to the microscope.

Figure 2:
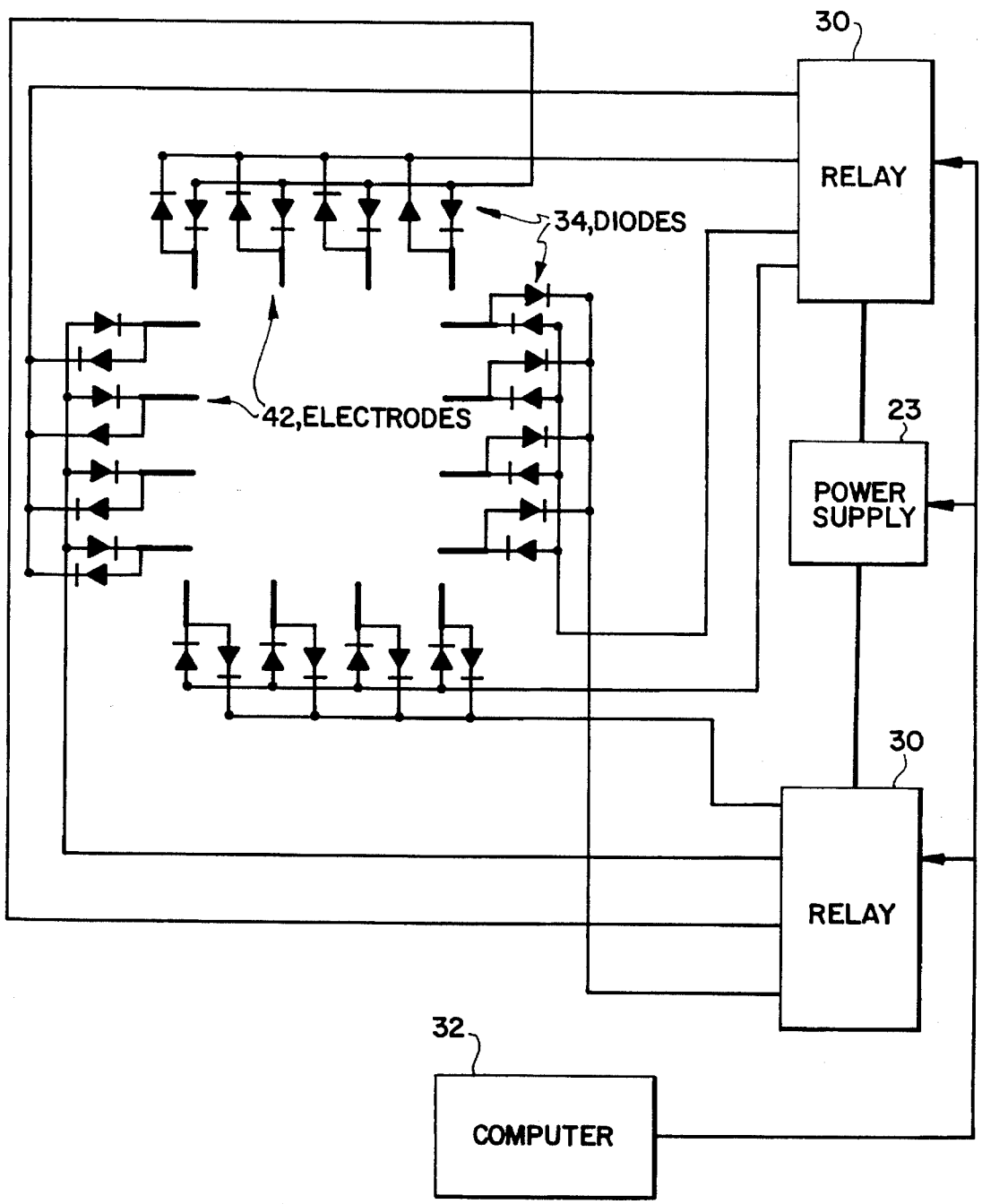
FIG. 2 is a partly schematic and partly block diagram showing an interconnection of exemplary chamber electrodes in an electrophoresis chamber which may be used in the present invention.

An exemplary laboratory instrument for POE is illustrated in FIG. 1 and a schematic view is shown in FIG. 2.

The instrument exemplified in FIG. 1 is similar to a miniature version of that described in U.S. Pat. No. 4,473,452, but differs in that the POE instrument has two sets of diodes 34 which enable bipolar operation of the discrete electrode array. The diodes 34 can be replaced by a multi-ganged relay (not shown) to provide similar electrical isolation. However, it is best to use the diodes 34 when very fast (less than 1 second) pulsing is needed.

As depicted in FIGS. 1 and 2, the miniature electrophoresis chamber 50 used in this invention measures about the size of a standard coverslip. It has electrodes 42', which are connected to diodes 34 (FIG. 2). In order to generate the desired electric fields, platinum electrodes 42' are interconnected as shown in FIG. 2. In particular, d-c power supply 28 supplies d-c power to relays 30, which are controlled by a computer 32 to connect selected outputs to the d-c power from power supply 28. Computer 32 also controls d-c power supply 28 so that the potential of the power supply can be varied. Outputs to relays 30 are connected to electrodes 42' through respective diodes 34 for each electrode.

As shown in FIG. 1, the miniature POE apparatus has a holder 52, which fits on a microscope stage. A slide 54, which holds an agarose gel, is placed into the holder and the electrodes 42 make electrical contact with the slide/gel/cover-slip sandwich placing drops of 30% glycerol-agarose at the agarose electrical connecting wicks 44. The glycerol prevents drying out of the gel. The electrical connector 46, which is part of the holder 52, provides a link to the bipolar diodes 34 and pulsing instrumentation shown in FIG. 2.

As in the case of the instrument described in U.S. Pat. No. 4,473,452, the presently exemplified instrument generates electrical fields which are orthogonal to each other, which alternate between high and low intensities out of phase with each other according to the chosen pulsing routine as described below and which translate the particles undergoing separation incrementally through the gel matrix in an overall direction transverse to the respective directions of the generated electrical fields. Due to the novel bipolar nature of the electrode design, it is possible to change polarities, simultaneously if desired, in addition to alternating high and low intensities without any significant electrode induced field distortions.

The determination of effective field angle by a pulsing routine rather than by placement of an electrode array permits molecular orientations (and separations) that would otherwise be difficult. As described in Example 4 below, POE has been used in DNA imaging experiments. The electrophoresis apparatus pictured in FIGS. 1 and 2 and used in Example 4 may be preferred over that of U.S. Pat. No. 4,695,548 because varying the field angle by moving electrodes as taught by conventional pulsed field electrophoresis is not practical due to microscope stage physical constraints. However, use of a POE device is not necessary to practice this invention when the molecules can be sufficiently perturbed by other means. Conventional electrophoresis using an apparatus which is about the size of a microscope slide is another preferred method for perturbing charged particles.

Figure 3A:
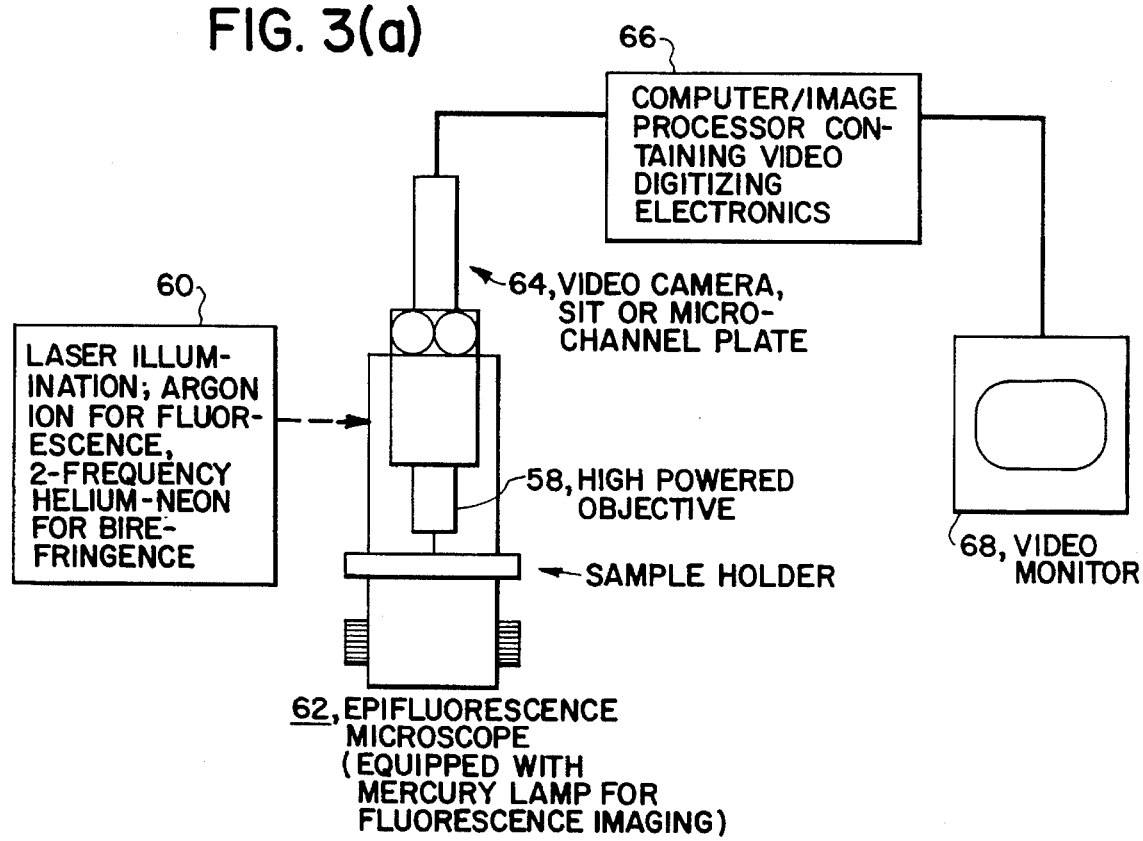
FIG. 3(a) is a schematic illustration of the instrumentation used in the microscopic study of DNA molecules in a medium according to this invention, and a more detailed diagram showing the instrumentation for measuring birefringence is illustrated in FIG. 3(b).

In a preferred embodiment of this invention, a small electrophoresis chamber containing polymer particles is placed upon a microscope slide and the polymer particles are viewed under a light microscope. As depicted in FIG. 3a, imaging of single molecules is accomplished with an epifluorescence microscope 62 (excitation light comes from above the sample as from laser 60) coupled to a low light level sensitive video camera 64 which is connected to an image processor 66, which in turn is connected to a video monitor 68. The use of epifluorescence microscopy here in this invention is an extension of the methodology first developed by Yanigida et al, in *Application of Fluorescence in the Biomedical Sciences,* (eds. Taylor, D. L. et al) 321–345 (Alan R. Liss, Inc., New York, 1986). A high powered oil immersion objective 58 is preferably used in the microscope. The key requirement is to use objectives with a high numerical aperture which gathers light effectively. A silicon intensified target (SIT) camera or a micro-channel plate detector is used to boost the light sensitivity to the point of counting photons. The image processor is a computer dedicated to digitizing, processing and storing images from the video camera. This type of image processor is known in the art. Images can be radically enhanced to bring up contrast, provide pseudocolor representation of grey levels (colors can be assigned to enhance images on an arbitrary basis, not unlike what is done with "colorizing" old black and white movies), and provide feature analysis which might include counting objects in the field of view. It is possible to view single DNA molecules stained with an appropriate chromophore, such as 4',6-diamidino-2-phenylindole dihydrochloride (DAPI), using epifluorescence microcopy.

The smallest size determination of this visualization technique is limited by microscope resolution, which, at this time, is approximately 0.1 microns or approximately 300 nucleotide bases in a DNA molecule. This length corresponds to the length of a small bacterial gene, however some DNA molecules are up to several inches in length, as is a human chromosome. Since it is possible to view several molecules in a sample simultaneously, it is also possible to measure sizes of many discrete molecules simultaneously.

An alternate way to size particles according to his invention involves measuring particles spectroscopically. This technique, when combined with microscopy, is particularly useful to size molecules which are too small to be imaged with satisfactory resolution and is described in detail in example 6. It also may be used for particles of medium or large sizes. Resolution using these techniques is simply limited by signal/noise as determined by photon counting.

The size parameters which are measured according to the preferred embodiments of this invention include relaxation or stretching rates of a perturbed particle, reorientation rate and/or rotation rate of a particle subject to perturbing forces in different direction, the curvilinear length of a perturbed particle, and the diameter of a spherical, ellipsoidal or globular particle. Each embodiment is based upon a mathematical relationship between the parameter which is measured and molecular size.

A first preferred embodiment involves measurement of the time required for a perturbed molecule to return to a relaxed state after application of an external force is terminated. The measurement of relaxation kinetics is described in Examples 1–4. This embodiment is based in part upon principles which mathematically relate relaxation time and molecular size.

An important advantage of measuring fragment sizes using relaxation rather than by other methods, such as measuring curvilinear length, is that the DNA molecules does not need to be totally stretched out in order to obtain an accurate measurement. The measured relaxation time is independent of the degree of coil extension. This has been clearly shown for measuring DNA relaxation times using the viscoelastic technique (Massa, D. J., *Biopolymers* 12:1071–1081 (1973)).

Figures 5A, 5B, 5C, 5D, 5E, 5F, 5G, 5H, 5I, 5J:
FIGS. 5a, 5b, 5c, 5d, 5e, 5f, 5g, 5h, 5i and 5j show the DNA molecular conformational and positional changes during relaxation of G bacteriophage DNA molecules after electrophoresis for 600 seconds, as revealed by the fluorescence microscopy experiments described in Example 4.

A second preferred embodiment involves measurement of the reorientation time of a molecule subject to at least one external force, for example, sequential electric fields in different directions. This is described below in Example 6 and is shown in FIGS. 4(a) and 5(j). The principles upon which reorientation rate is based have been studied by the inventor using fluorescence microscopy/image processing. Using the process as described below in the Examples, it has been determined that during pulsed field electrophoresis, the blob train of a DNA molecule orients with the applied electric field in a very complicated manner and during this process, electrophoretic mobility is retarded until alignment is complete, e.g., until the molecule is aligned with the applied field. Upon field direction change, the blob train moves in several new directions simultaneously (i.e., the blobs appear to be moving somewhat independently). Eventually, some part of the blob train dominates in reorienting with the applied field and pulls the rest of the blobs along its created path through the gel. The time necessary for complete blob train alignment varies directly with size; i.e., a 10 mb (1 mb=1,000 kb) molecule requires one hour to reorient, while a 10 kb molecule requires only ten seconds, using similar field strengths. The phenomenon is illustrated in FIG. 4. Reorientation is measured in various ways, including by light microscopy and by microscopy combined with spectroscopic methods.

A third preferred embodiment of this invention involves measurement of the rotation time of a molecule subject to sequential electric fields in different directions. In one sense, rotation of a molecule requires a series of incremental reorientation steps, each of which causes the particle to rotate further in the same direction, until the particle has undergone a rotation of a specified angular increment, for example, 360°. This embodiment is particularly well suited to characterize stiff, rod-like particles, such as small DNA molecules, which do not significantly change conformation upon application of an external force. However, large molecules also may be sized by this method if the conformation of the molecules is kept fairly constant, preferably in a rod-like or elongated conformation. This is accomplished by applying a pulsing routine which is appropriate to the size, shape and perhaps also the composition of the molecule.

As a non-limiting example, molecules are rotated in the presence of sinusoidally varying electrical fields applied at 90° to each other. Stiff, rod-shaped molecules or stretched molecules are rotated about the long or short axis. Rotation about the long axis has the greatest molecular weight dependence, with rotation diffusion varying as about $M^3$. Rotational motion of a rod-shaped molecule immersed in a gel or any other confining may be difficult if an attempt is made to simply rotate the molecule as a boat propeller rotates in water. When a gel is used, the matrix affects rotation of the molecule much as seaweed affects the rotation of a boat propeller. Thus, a pulsing routine is applied which also provides back and forth motion of the particle, thereby facilitating rotation.

The pulsing routine may be defined by an algorithm. Generally speaking, the algorithm may depend on variables such as angle increment, time, electric field intensity, etc., and these may in turn be a function of different variables. Thus, the types of usable algorithms are numerous.

A preferred pulsing routine for this invention may be defined as follows:

$$\vec{E}_1(t) = E(t, \Theta_i)(\hat{i}\cos\Theta_i + \hat{j}\sin\Theta_i)(\Delta t)$$

$$\vec{E}_2(t) = E(t, \Theta_i)(\hat{i}\cos(\Theta_i + \pi) + \hat{j}\sin(\Theta_i + \pi))(\Delta t)$$

$$P_i = k_1 \cdot \vec{E}_1(t), k_2 \cdot \vec{E}_2(t), k_1 \cdot \vec{E}_1(t)$$

wherein:

$\vec{E}_{1(t)}$ and $\vec{E}_{2(t)}$ are electric field vectors multiplied by time (volt.sec/cm);

$E(t, \Theta_i)$ is the electric field intensity in volt/cm;

$\hat{i}$ and $\hat{j}$ are unit vectors;

$\Theta_i$ is the field angle, in radians or degrees, with $i=1 \to n$, where $$\sum_{i=1}^{n} \Theta_i = 2\pi \text{ or } 360°,$$

for a complete rotation;

$\Delta t$ is pulse length, in seconds;

t is time in seconds;

$k_1$ and $k_2$ are the number of successive identical pulses; and

P is a pulsing routine, which may be repeated.

Using the above routine, a particle to which appropriate pulses are applied rotates about $(\Theta_{i+1}-\Theta_i)$ radians or degrees when each set of pulses P are initiated. Also, the molecule is translated (moves laterally) in the directions of $\vec{E}(t)$ and $-\vec{E}(t)$, thereby facilitating rotation.

In the above equation, $\Delta t$ is a constant, however, this need not be the case. $\vec{E}$ may be a function of any variable or set of variables. For example, E may be a function of total elapsed time and/or angle increment. Also, the sum of all the angular increments need not be 360°, and may be any number of partial or total rotations which provide measurements of sufficient accuracy.

A specific set of conditions for measuring the rotation rate of molecules are set forth in Example 7.

According to a fourth preferred embodiment of this present invention, a useful way to measure the size of particles such as polymer molecules is to visualize them and measure their curvilinear length (equivalent to measuring the length of a rope) directly using a light microscope. It is shown in Example 4 below, and in FIGS. 4a to 4i and 5a to 5j, that fluorescence microscopy can image single polymer molecules stained with an appropriate chromophore. Incredibly, even though the polymer diameter dimensions may be only just 20 angstroms, single molecules are easily visualized. If the molecule is stretched out and a computerized imaging apparatus is used to measure the length of the visualized molecule, the size dependence of the measurements varies as about $M^1$. Measurements of length are particularly useful in sizing and ordering DNA fragments, such as restriction digests, as described in detail in Example 10.

A fifth preferred embodiment involves measuring the diameter of a relaxed particle. Measurements of molecular diameter are made according to the same procedure of staining molecules, placing the molecules in a medium, etc. as the curvilinear length measurements. However, it is not necessary to perturb the molecules before measurement. Instead, the molecules are measured when they are in a relaxed state, having a spherical or elongated elliptical shape. Because the volume of a sphere is proportional to $R^3$ where R=radius, and the volume of an ellipsoid is proportioned to $ab^2$ where a is the radius of the major axis, and b is the radius of the shorter axis, resolution for this technique varies as about $M^{.33}$. Particles measured by this technique do not need to be deformable. This technique can be used for all sizes of DNA molecules and is useful for sizing large DNA molecules, which can now successfully be mounted on a microscope slide, as well as for sizing densely packed molecules.

Large particles, such as large DNA molecules, are difficult to mount on a microscope slide without causing breakage, and the inventor addresses this problem using a novel technique, which is a further aspect of this invention. A typical human chromosome may contain a single DNA molecule stretching inches in length. Nature provides a clever packaging scheme to fit approximately six feet of DNA into a cell measuring only a few microns in diameter. However, these large DNA molecules are very sensitive to breakage. For example, solutions of large DNA molecules cannot be poured, pipetted, or stirred without breaking molecules. Thus, working with large DNA molecules can be very difficult. Some years ago the inventor developed a gel based method of preparing large DNA molecules without breakage that also permitted biochemistry using intact molecules, (see U.S. Pat. No. 4,695,548). The procedure is called the insert method and works as follows: Cells are washed and mixed with low gelling temperature agarose kept at 37° C. The cell-agarose mixture is pipetted into a mold (to produce small blocks to fit into the wells of a slab gel) and allowed to gel. The resulting blocks or "inserts" as they are named are then placed into a lysis solution containing EDTA, protease and detergent. The lysis solution diffuses into the insert, lyses the cells and renders intact naked DNA molecules stripped of their associated proteins. The DNA molecules do not diffuse out of the insert because very large coils are generally unable to diffuse.

The inventor has found that DNA molecules up to at least megabase (1 megabase=1 million bases=$660 \times 10^6$ daltons) when suspended in liquid agarose are protected against shear when mounted on a microscope slide. However for molecules larger than 2 or 3 megabases or for situations where the integrity of 100% of the molecules must be ensured, this procedure is not effective.

A sixth embodiment of the invention remedies the above-mentioned problem involved in placing molecules larger than 1 megabase on a microscope slide. The inventor developed a protocol using a condensation agent to collapse gel bound DNA (as obtained from inserts) into small shear resistant balls, that can be unfolded once mounted, with the addition of an ionic compound, for example, a salt such as sodium chloride or magnesium chloride. Preferably, the condensation agent is spermine. The spermine protocol, which is described further in Example 10, permits the mounting of DNA molecules of even the largest known DNA molecules, and feasibly even larger molecules, without any detectable shear mediated breakage. While the use of spermine is preferred, other suitable materials for collapsing the molecule include any material which can cause a particular particle to collapse, e.g., any condensation agent which causes particles to preferentially solvate themselves. Examples of such materials include, but are not limited to spermidine, alcohol and hexamine cobalt.

A seventh preferred embodiment of the invention relates to a specific application of the above embodiments of this invention to map DNA molecules using restriction enzymes. The previously known method for constructing a restriction map is to incubate DNA with a restriction enzyme and size separate the resulting fragments using conventional gel electrophoresis or pulsed electrophoresis. Size separation provides information on the number and size of the fragments but no information on the relative location of fragments or cutting sites on the uncut DNA molecule. By using the microscope to image molecules undergoing digestion by restriction enzymes, (1) size resolution is accurately determined by measuring relaxation kinetics, (2) positioning of fragments relative to each other can be determined, and (3) only one molecule needs to be digested (however, many molecules can be image processed in parallel). The only limitation is space on the sample holder.

In brief, restriction mapping using the microscope involves mounting large gel embedded DNA molecules on a microscope slide, stretching them to some extent (it is not necessary that the molecules be completely stretched), and then inducing cleavage. The fragment positions are noted and their sizes are determined using the methods outlined in embodiments one to four, using visualization or spectroscopy. A preferred embodiment of this aspect of the invention is described in detail in Example 11.

An eighth preferred embodiment of this invention relates to mapping nucleic acid sequences using hybridized probes. With this technique, a nucleic acid, a probe (a characterized nucleic acid) and under certain circumstances, a recombinational enzyme, are combined in a matrix. The probe may be of any practical length and may be labelled with any suitable labelling agent. If a recombinational enzyme is used, (e.g., if the probe is not capable of invading the target molecule without the use of a recombinational enzyme) it may be any suitable enzyme, for example, one known in the art for conventional labelling of DNA probes. As a non-limiting, specific example, a useful recombinational enzyme is recA.

Hybridization can be initiated by any suitable means, for example, by diffusing ATP and magnesium ions into the microscope slide.

Probes can be hybridized to a target molecule and visualized in at least two different ways. First, the probe may be visualized directly if it is sufficiently large. For example, a probe larger than 1 kb probably can be visualized using microscopy equipment which is currently available. Second, a chromophore, or other suitable labelling agent can be attached to the probe and can be detected visually or spectroscopically. For example, Texas Red or rhodamine, as well as other chromophores, may be used.

After the probe has been hybridized to the target molecule, there are at least two preferred ways to map the position of the probe. However, other methods are also within the scope of this invention. As a first preferred alternative, the curvilinear length of the target molecule can be measured. When a light microscope is used, fluorescence intensity measurements can be used to locate and quantify linear regions which are not totally stretched out. The position of the probe is located based upon its characterizing feature, e.g., chromophore, radioactive tag, and/or size.

As a second preferred alternative, a target molecule is cut with restriction enzymes and all of the fragments are sized and measured by the methods of this invention. The location of the hybridized fragment is determined by one of the methods described above, e.g., by direct visualization of the molecule or by microscopy combined with spectroscopic techniques. All of the fragments are sized, and the distance from the labelled fragment to either end of the target molecule is then easily calculated. The exact position of the probe on a particular restriction digest can be mapped with the addition of a new enzyme for further digestion, and these fragments can then be mapped visually.

In summary, the medium-based sizing process of this invention involves characterization of particles using a microscope. Particles, particularly small or medium-sized molecules, are placed in a medium and mounted on a slide using conventional techniques. Large molecules are mounted on a microscope slide using spermine condensation, which avoids breakage problems. At some point the molecules may be stained. The molecules may be perturbed in the medium by the application of an electrical field. The field is then shut off, allowing the molecules to relax to their equilibrium conformation, which on the average is spherical or ellipsoidal, or to assume a certain position. An image processor connected to a video camera counts the molecules and follows their shape changes. The kinetics of relaxation, reorientation and rotation of the molecules, as well as their length and diameter are calculated automatically, and molecular weights for all of the imaged molecules are calculated from established relationships.

The following examples are offered in order to more fully illustrate the invention, but are not to be construed as limiting the scope thereof.

EXAMPLE 1

Preparing DNA for Microscopy

G bacteria was grown as described by Fangman, W. L., *Nucl. Acids Res.*, 5, 653–665 (1978), and DNA were prepared by lysing the intact virus in ½× TBE buffer (1×: 85 mM Trizma Base (Sigma Chemical Co., St. Louis Mo.), 89 mM boric acid and 2.5 mM disodium EDTA) followed by ethanol precipitation; this step did not shear the DNA as judged by pulsed electrophoresis and microscopic analysis.

DNA solutions (0.1 microgram/microliter in ½×TBE) were diluted (approximately 0.1–0.2 nanogram/µl agarose) with 1.0% low gelling temperature agarose (Sea Plaque, FMC Corp., Rockport, Me.) in ½× TBE, 0.3 micrograms/ml DAPI (Sigma Chemical Co.), 1.0% 2-mercaptoethanol and held at 65° C. All materials except the DNA were passed through a 0.2 micron filter to reduce fluorescent debris. Any possible DNA melting due to experimental conditions was checked using pulsed electrophoresis analysis and found not to be a problem.

EXAMPLE 2

Imaging DNA in a Gel

The sample of Example 1 was placed on a microscope slide. To mount the sample, approximately 3 microliters of the DNA-agarose mixture were carefully transferred to a preheated slide and cover slip using a PIPETTEMAN™ and pipette tips with the ends cut off to reduce shear. Prepared slides were placed in a miniature pulsed electrophoresis apparatus as shown in FIGS. 1 and 2. All remaining steps were performed at room temperature. Samples were pre-electrophoresed for a few minutes and allowed to relax before any data was collected. Pulsed fields were created with either a chrontrol time (Chrontrol Corp., San Diego, Calif.) or an Adtron data generating board (Adtron Corp., Gilbert, Ariz.) housed in an IBM AT computer and powered by a Hewlett Packard 6115A precision power supply. Field Strength was measured with auxiliary electrodes connected to a Fluke digital multimeter (J. Fluke Co., Everett, Wash.). A Zeiss Axioplan microscope (Carl Zeiss, West Germany) equipped with epifluorescence optics suitable for DAPI fluorescence and a Zeiss 100× Plan Neofluar oil immersion objective was used for visualizing samples. Excitation light was attenuated using neutral density filters to avoid photo-damage to the fluorescently labeled DNA. A C2400 silicon intensified target (SIT) camera (Hamamatsu Corp., Middlesex, N.J.) was used in conjunction with an IC-1 image processing system (Inovision Corp., Research Triangle Park, N.C.) to obtain and process video images from the microscope. Images were obtained continuously at the rate of one every five or six seconds, and as many as 200 digitized images could be stored per time course. Each digitized time-lapse image benefitted from the integration of 8 frames obtained at 30 Hz, which was fast enough to avoid streaking due to coil motion. After the time-lapse acquisition was complete, the microscope was brought out-of-focus and a background image was obtained. Each time-lapse image was processed by first attenuating a copy of the background image, so that the average background intensity was 82% of the average time-lapse image intensity. The attenuated background was subtracted from the time-lapse image and the resultant image was then subjected to a linear-stretch contrast enhancement algorithm. Photographs of the processed images were obtained using a Polaroid Freeze Frame video image recorder (Polaroid Corp., Cambridge, Mass.).

EXAMPLE 3

Perturbing Molecules in a Gel

The molecules of Example 2 were perturbed by POE. POE was accomplished by using a series of relatively short normal pulses of a chosen ratio and then after a longer time period, the polarity of one of the fields was switched. The switch time and normal field ratio are analogous to the pulsed electrophoresis variables of pulse time and field angle.

The nomenclature used to describe a POE experiment is as follows: 3,5–80 second pulses, 3 volts/cM). "3,5–80 seconds" means a 3 second pulse south-north, followed by a 5 second pulse east-west; after 80 seconds of this 3,5 second cycle, the polarity of the 5 second pulse is changed (west-east) for another 80 seconds, and a zig-zag staircase path is defined for the molecules involved. The pulse intensity was 3 volts/cM.

In this Example, epifluorescence microscopy was coupled with the POE method to enable the general study of DNA conformational and positional changes during electrophoresis. While the POE method using the adapted microscopy chamber shown in FIG. 2 was used in this experiment, ordinary electric fields switched on and off could have been used. POE offers certain advantages when electric fields are to be applied at different angles, as may be needed to rotate a molecule about its long axis.

FIGS. 1 and 2 show diagrams of the adapted POE chamber.

EXAMPLE 4

Observing and Measuring Molecular Relaxation in a Gel

The relaxation of the G bacteriophage DNA of Examples 1–3 was observed after POE was conducted for 600 seconds (3,5–80 second pulses, 3 volts/cm).

The image processor is used to quantify and automate the imaging of the relaxation process, for example, through "feature analysis". Feature analysis works after successive images have been digitized and stored, as shown in FIG. 3(a). The image processor then identifies discrete objects in the images, numbers them, and characterizes them according to shape. For example, the computer determines the effective ellipsoid axes (long and short) for a collection of distorted coils and calculates these features as a function of time as the coil approaches a spherical conformation during the relaxation process. Other types of computerized measurements also can be made to characterize the DNA.

The images displayed in FIG. 5, obtained at 12 second intervals, show the relaxation of several molecules over a 96 second time span. In (a), several coils are shown 3 seconds after the applied field was turned off. The coils appear to relax through the same corrugated staircase path defined by the applied electrical pulses (see molecules marked by arrows) as determined by the limits of microscopic resolution. In (c), a molecule is shown splitting into two, and by (j), all coils have relaxed to a round, unelongated conformation. The bar shown in (j) is 10 microns in length.

EXAMPLE 5

Determining the Molecular Weight of One or More Molecules by Measuring Relaxation Kinetics Molecules of known molecular weight are prepared for imaging according to the procedures of Examples 1–3, and the relaxation time of the molecules is determined by the methods of Examples 1–4. Relaxation time data is collected by imaging and is used to calculate a mathematical relationship between molecular weight and relaxation time of DNA molecules of similar composition. The relaxation time of a sample of molecules of unknown size is then measured, and the size of the molecules is calculated using the mathematical relationship determined on the basis of molecules of known size.

EXAMPLE 6

Determining the Molecular Weight of One or More Molecules by Measuring Reorientation Rate in a Gel Polymers of any size, but particularly those that are too small to image (less than approximately 0.1 micron), are sized in a matrix such as agarose or polyacrylamide gel by measuring the reorientation rate as induced by an applied electrical field. Although a reorientation measurements could be done in free solution, a matrix is preferred because it prevents unnecessary polymer convection and movement. Additionally the presence of a matrix may enhance the size sensitivity, partly because the orientation mechanism is different. POE is particularly useful for measuring reorientation time because of its experimental versatility and very high size resolution of perhaps 15 to 20 megabases. Stiff polymers such as DNA molecules (sized less than 150 base pairs) exist in solution as rods and the rotational diffusion coefficient (the friction felt by the rod as you try to spin about its long axis) varies as $M^3$. Using microscopy, molecules which are large enough to be imaged are visualized, and their reorientation time is determined from the images. For any size of molecules, particularly those which are too small to visualize, the reorientation time of each rod in the field of view is preferably measured by spectroscopic methods. Two such methods are described in detail below, namely fluorescence dichroism and birefringence:

1) A chromophore that binds in a sterically predictable way (ethidium bromide intercalates into DNA molecules) is attached to a polymer molecule. Polarized radiation is used to excite the chromophore. Measuring the total fluorescence intensity temporally provides orientation information of each molecule. The fluorescence radiation of each molecule in the microscope field is measured using a sensitive microchannel plate detector.

2) The orientational dynamics of a molecule is followed with birefringence measurements. Birefringence techniques measure the change of refractive index, which is easily correlated with the orientation of macromolecules in solution or in a matrix. Birefringence measurements are taken while the DNA molecules are undergoing gel electrophoresis. When an electrical field is applied, the DNA molecules stretch out and align with the field, thereby changing the refractive index. By measuring the change of birefringence with time, it is possible to understand details of DNA blob train motion as the molecule orients with the applied electrical field.

Figure 3B:
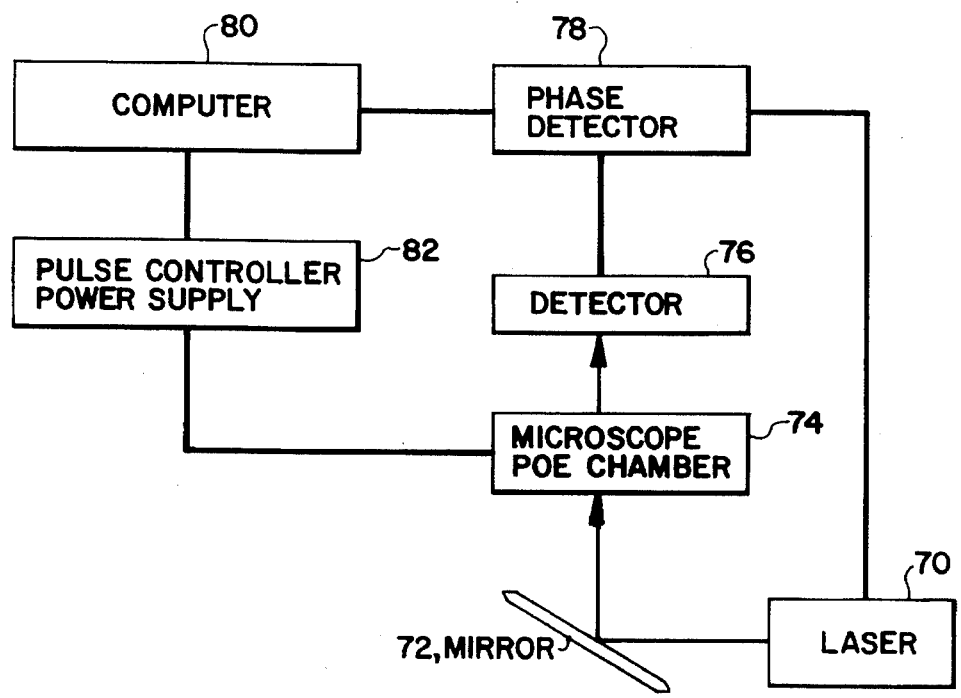

More specifically, birefringence measurements are made by determining the phase difference of two orthogonally polarized planes of laser radiation (red light) differing by a small frequency difference (supplied by the two frequency laser). As the molecules align with the applied electrical field (in the POE chamber), which is generated by pulse controller 82, the refractive index changes with molecular alignment. Light is detected by detector 76, and results in a phase difference in the transmitted radiation, which is measured by the phase detector 78 (FIG. 3(b)) by comparing the value to a standard, sourced at laser 70. The phase difference data obtained as a function of time (the period of field application) is digitized and stored on computer 80 for later retrieval and analysis.

The instrument depicted in FIGS. 1 and 2 applies the necessary fields to cause molecular reorientation. Many different rotational schemes can be described to optimally size molecules in the field. For example, the rotating field frequency can be swept to find resonant frequencies with the polymer sample.

EXAMPLE 7

Determining the Molecular Weight of One or More DNA Molecules by Measuring the Rotation Time of the Molecules in a Gel Molecules in the shape of rods or stiff coils are prepared and observed as in Examples 1–4, except that an acrylamide, rather than agarose gel optionally may be used.

The rate of rotation of a coil or a rod is measured with a microscope-based system using any one of the techniques described above in Example 6. Measurements are made of a sinusoidally varying signal as the molecule spins about its center. The sinusoidal signal is used to determine the polymer size or molecular weight by fitting the period of the sinusoidal signal to the rotational frictional coefficient, which varies as the cube power of the rod length. In other words, the measured angular velocity as measured from the sinusoidal signal (radians/sec.) varies as the rod length cubed in free solution (Boersma, S. (1960) J. Chem Phys. 32: 1626–1631, 1632–1635).

The conditions for a proposed series of experimental runs, with constant t, are shown below.

| M Molecular size (base prs or kilo bases) | E Electric Field Strength (volt/cm) | $\Delta t$ Duration angle (in of each Pulse (Sec) | $\Theta_r$ Inclemental clockwise direction (Deg.) |
|---|---|---|---|
| 50 bp | 5 | $1 \times 10^{-4}$ | 10 |
| 150 bp | 5 | $1 \times 10^{-4}$ | 10 |
| 50 kb | 5 | 1 | 10 |
| 500 kb | 5 | 5 | 10 |
| 500 kb | 5 | 900 | 10 |

Thus, in the first example, pairs, triplets or other sets of pulses of 5 volts/cm are successively applied for 0.1 millisecond in opposite directions, with the direction of the first of each successive set of pulses increasing by 10 degrees in a clockwise direction away from the starting point.

Molecules of known molecular weight are placed in a gel, and their rotation rate is determined when the above-described electric fields are applied. Rotation time data is collected and is used to calculate a mathematical relationship between molecular weight and rotation time of G bacteriophage DNA molecules in a particular gel. The rotation time of molecules of unknown size is then measured, preferably using a similar electric field, and the size of the molecules is calculated using the mathematical relationship determined on the basis of molecules of known size.

EXAMPLE 8

Determining the Molecular Weight of One or More Molecules by Measuring Curvilinear Length of DNA Molecules in a Gel The procedure of Examples 1–4 is followed for molecules of known molecular weight. Measurements of the curvilinear length of the molecules while they are in a perturbed state is collected by visualizing the molecules and is used to calculate a mathematical relationship between molecular weight and length. The curvilinear length of perturbed molecules of similar composition and unknown size is then measured using the procedures of Examples 1–4, and the size of the molecules is calculated using the mathematical relationship determined on the basis of molecules of known size. FIGS. 4b to 4i and 5b to 5j show perturbed molecules for which curvilinear length measurements can be made.

EXAMPLE 9

Determining the Molecular Weight of One or More Molecules by Measuring Diameter of DNA Molecules in a Gel The procedure of Examples 1–4 is followed for molecules of known molecular weight, except that measurements are made when the molecules are in a completely relaxed state. Measurements of the diameter or diameters of the substantially spherical or ellipsoidal G bacteriophage DNA molecules are collected and are used to calculate a mathematical relationship between molecular weight and diameter of G bacteriophage DNA molecules in the gel. The diameter of molecules of unknown size is then measured, and the size of the molecules is calculated using the mathematical relationship determined on the basis of molecules of known size. FIGS. 4(a) and 5(j) show relaxed molecules for which diameter measurements can be made.

EXAMPLE 10

Preparing Large DNA Molecules for Imaging

Chromosomal DNA molecules from *Saccharomyces cerevisiae* were prepared and isolated using the insert method and pulsed electrophoresis. Low gelling temperature agarose gel (FMC Corp. Rockland, Me.) was used for preparation to permit relatively low temperature melting. Since UV radiation can break DNA molecules, desired bands were cut out of the gel, guided by ethidium stained flanking edge sections that were cut out of the gel, which were then photographed on a 301 nm transilluminator apparatus. The bands were then weighed and equilibrated with a 10-fold excess of 10 mM spermine in water for 3 hours at room temperature. Spermine requires a very low ionic strength environment to condense DNA and, fortunately, the buffers used in electrophoresis are low ionic strength, thus eliminating the need for an equilibration step. The equilibrated samples were then melted in an oven at 74° C. for two hours and after melting, DAPI (1 microgram/ml) and 2-mercaptoethanol (1%) were added. 3 microliters of the melted agarose/DNA mixture were carefully applied to a pre-heated microscope slide and a cover slip was placed on top before the mixture gelled. The slide was then viewed using a Zeiss Axioplan epifluorescence microscope fitted with a 100× Plan Neofluar objective and showed small intensely bright balls which could be decondensed by the addition of salt, through the edges of the coverslip sandwich.

As mentioned above, spermine is particularly useful in an environment of low ionic strength. On the other hand, if DNA molecules are placed in a highly ionic environment, the same type of condensation effect are accomplished with alcohol. Neither of these examples are to be construed as limiting the scope of the invention.

EXAMPLE 11

Restriction Mapping *Schizosaccharomyces pombe* Chromosomal DNA Molecules

The DNA of *Schizosaccharomyces pombe,* a fungus with a genome size of about 17–19 megabases distributed on three chromosomes 3, 6 and 8–10 megabases in size, is prepared for microscopy by condensation and uncollapsing, according to the method of Example 10. The 3–5 microliter agarose mixture contains approximately 0.1 nanograms of DNA, 0.5% b-mercaptoethanol, 1 microgram/ml DAPI, 100 micrograms/ml bovine serum albumin (acetylated; Bethesda Research Laboratories, Gaithersburg, Md.) and 10–20 units of an appropriate restriction enzyme. This mixture is briefly held at 37° C. and carefully deposited on a microscope slide and then topped with a coverslip. Prior to digestion with restriction enzymes the DNA is stretched by one of two ways: (1) the liquid slide/agarose/coverslip sandwich is optionally sheared slightly by moving the coverslip or (2) an electrical field is applied using, for example, the POE instrument described in FIG. 3(*a*). A 10 mM magnesium chloride solution is then diffused into the sandwich once the gel has set. When the magnesium ions reach the DNA/enzyme complex, the enzyme cleaves the DNA molecule.

The positions of the restriction cutting sites are determined by following the DNA strand from one end to the other using the microscope setup and noting cut sites. These sites appear as gaps in the strand, which is continuous before enzymatic digestion. The size of each of the fragments is then determined by the microscopic methods of this invention, including, (1) measuring the curvilinear length of each fragment, (2) allowing the fragments to relax and measuring their diameter, (3) perturbing the conformation of each fragment with an applied electrical field or flow field (as generated by moving solvent through a gel) and measuring the relaxation kinetics with direct visual detection of conformational and positional changes or microscopy combined with spectroscopy. Direct visual observation is preferred for larger molecules, while the other methods are well suited for fragments too small to image.

The resulting sample when viewed using a fluorescence microscope shows a number of bright balls of three different sizes, with diameters varying as $M^{.33}$ which is based upon the formula for the volume of a sphere, $4/3\pi R^3$. The gel also contains a restriction enzyme which is active only when magnesium ions are present.

EXAMPLE 12

In situ Hybridization of Nucleic Acid Probes to Single DNA Molecules

Nucleic acids are prepared for microscopy as described in Examples 1–4 above. The agarose medium containing the nucleic acid particles also contains labelled probes and a recombinational enzyme, recA, which mediates strand displacement of the target molecule by the probe. Strand displacement and pairing occurs by D-looping (see Radding, C., *Ann. Rev. Genet.* 16:405–37 (1982)). ATP and magnesium ions are added to begin the reactions. These ingredients are diffused into the slide/gel/coverslip sandwich as described in Example 11. The reaction is incubated at 37° C. Many different target molecules are simultaneously analyzed, using probes with different labels.

Variations of the method of this invention other than those specifically described above are within the scope of the invention. For example, other parameters of the molecules can be measured, and various type of microscopes and spectroscopic equipment may be used. The pulsing routines for effecting particle rotation can be varied. Combinations of the above-described techniques are also contemplated. For example, combinations of various types of external forces, mediums and spectroscopic techniques are within the scope of the invention. Furthermore, a measuring technique may be repeated several times, and the measurements from each trial may be averaged.

I claim:

1. A method for characterizing single, isolated nucleic acid, including any molecules specifically bound thereto, comprising the steps of:

placing said nucleic acid in a medium, applying a temporary external force in a repeatable, controlled fashion to said nucleic acid, said force being of a type which causes a molecular size-dependent measurable change in said nucleic acid, wherein said change comprises a conformational change or a change in position, observing said nucleic acid using a microscope:

measuring said change using the microscope; and determining the molecular size of said nucleic acid based on said change measured using the microscope.

2. The method of claim 1 wherein said change comprises a conformational change, and the rate of change after termination of said force is measured.

3. The method of claim 1 wherein said change comprises a conformational change, and the rate of change after initiation of said force is measured.

4. The method of claim 1 wherein said change comprises a positional change, and the rate of change after initiation of said force is measured.

5. The method of claim 4 wherein said positional change comprises a rotational change and optionally comprises lateral movement, and a rate of said positional change after initiation of said force is measured.

6. The method of claim 1 further comprising the step of collapsing said nucleic acid before placement in said medium.

7. The method of claim 6, wherein said nucleic acid is shear sensitive.

8. The method of claim 6, further comprising the step of uncollapsing said nucleic acid after placement in said medium.

9. The method of claim 8 wherein said nucleic acid is collapsed using a condensation agent, and is uncollapsed using an ionic substance.

10. The method of claim 9, wherein said condensation agent comprises spermine, spermidine, alcohol or hexamine cobalt.

11. The method of claim 1, wherein said medium comprises at least one of a solution, gel, powder and glass.

12. The method of claim 1, wherein said nucleic acid is labelled with a labelling agent before it is measured.

13. The method of claim 12, wherein said labelling agent comprises a stain.

14. The method of claim 1 wherein said microscope is a light microscope.

15. The method of claim 1, wherein said medium is a matrix.

16. The method of claim 15 further comprising the step of collapsing said molecule before placement in said matrix.

17. The method of claim 16, wherein said molecule is shear sensitive.

18. The method of claim 17 further comprising the step of uncollapsing said molecule after placement in said matrix.

19. The method of claim 18 wherein said molecule is collapsed using a condensation agent, and is uncollapsed using an ionic substance.

20. The method of claim 1, wherein said measuring and determining steps further comprise using the microscope linked to a computerized image processor.

21. A method for determining the molecular weight of single, isolated nucleic acid of unknown size, comprising the steps of:

placing a first nucleic acid of predetermined size in medium;

applying a temporary external force in a repeatable, controlled fashion to said first nucleic acid of predetermined size, said force being of a type which causes a molecular size-dependent measurable change in said first nucleic acid of predetermined size, wherein said change comprises a conformational change or a change in position;

observing said first nucleic acid of predetermined size using a microscope;

measuring said change using the microscope;

placing a second nucleic acid of predetermined size in a medium;

applying a temporary external force in a repeatable, controlled fashion to said second nucleic acid of predetermined size, said force being of a type which cause a molecular size-dependent measurable change in said second nucleic acid of predetermined size, wherein said change comprises a conformational change or a change in position;

observing said second nucleic acid of predetermined size using the microscope;

measuring said change using the microscope;

placing a nucleic acid of unknown size in a medium;

applying a temporary external force in a repeatable; controlled fashion to said nucleic acid of unknown size, said force being of a type which causes a molecular size-dependent measurable change in said nucleic acid of unknown size, wherein said change comprises a conformational change or a change in position;

observing said nucleic acid of unknown size using the microscope;

measuring said change using the microscope;

calculating a mathematical relationship between the size and rate of change of each of said nucleic acids of predetermined size; and determining the size of said nucleic acid of unknown size.

22. A method for characterizing a single, isolated nucleic acid, comprising the steps of:

placing said nucleic acid in a medium;

placing in said medium a recombinational enzyme and a labelled probe that hybridizes to a portion of said nucleic acid, wherein said recombinational enzyme facilitates the hybridization of the labelled probe to a portion of said nucleic acid;

hybridizing said probe to said nucleic acid, whereby a complex is formed;

observing said nucleic acid using a microscope; and mapping said complex using the microscope.

23. A method for mapping a deproteinized, single, isolated nucleic acid or a portion thereof, comprising the steps of:

placing in a medium said nucleic acid and a probe to a portion of said nucleic acid;

inducing hybridization;

observing said nucleic acid using a microscope; and characterizing said hybridized nucleic acid using the microscope.

24. The method of claim 23, further comprising contacting said nucleic acid with a recombinational enzyme to facilitate hybridization of said probe to a portion of said nucleic acid under conditions such that said hybridization occurs.

25. The method of claim 24, wherein said probe is labelled.

26. A method for sizing and mapping a single, isolated nucleic acid molecule, comprising the steps of:

i) placing said molecule in a medium;

ii) contacting said molecule with at least one restriction enzyme under conditions such that restriction digestion occurs, whereby fragments are produced;

iii) observing said digestion using a microscope;

iv) applying a temporary external force to said fragments, said force being of a type that causes a molecular size-dependent measurable change in said fragments;

v) measuring said change using the microscope; and vi) determining the molecular size of said fragments based on said change measured using the microscope.

27. The method according to claim 26 wherein said nucleic acid is mounted on a microscope slide and stretched prior to said restriction digestion.

28. The method of claim 26 wherein said change is a conformational change.

* * * * *